United States Patent [19]

Carney et al.

[11] 4,333,918

[45] Jun. 8, 1982

[54] RADIOASSAY FOR VITAMIN $B_{12}$

[75] Inventors: James A. Carney, London, England; Adrienne R. McGregor, East Malvern, Australia

[73] Assignee: Technicon Instruments Corporation, Tarrytown, N.Y.

[21] Appl. No.: 969,624

[22] Filed: Mar. 23, 1979

[51] Int. Cl.³ .................... G01N 33/54; G01N 33/56; G01T 1/00
[52] U.S. Cl. ....................................... 424/1; 23/230 B; 424/12
[58] Field of Search ................... 424/1, 12; 23/230 B

[56] References Cited
U.S. PATENT DOCUMENTS 3,937,799 2/1976 Lewin et al. ............................ 424/1
4,146,602 3/1979 Gutcho et al. ........................ 424/12
4,188,189 2/1980 Allen ...................................... 424/1

*Primary Examiner*—Christine M. Nucker
*Attorney, Agent, or Firm*—S. P. Tedesco

[57] ABSTRACT

The amount of vitamin $B_{12}$ in solution in a liquid is determined by mixing a sample of the solution with vitamin $B_{12}$-binding proteins from chicken serum in a pH of about 12.8 to 13.2, and then analyzing a component of the mixture. In preferred procedures, especially useful in assaying human sera, a competitive binding technique is employed utilizing labelled vitamin $B_{12}$ and a buffer containing cyanide ion. By operating at very high pH and with chicken serum proteins, the assay can be conducted relatively simply and with very accurate results.

13 Claims, 3 Drawing Figures

RADIOASSAY FOR VITAMIN $B_{12}$

This invention is concerned with a method of assaying fluids for their vitamin $B_{12}$ content (hereinafter vitamin $B_{12}$ is referred to as "$B_{12}$"). The method of the invention is particularly, though not exclusively, useful in the assay of biological fluids such as human serum.

It is important for medical purposes to be able accurately to assay human serum for its $B_{12}$ content. For example, the $B_{12}$ content of normal serum may range from about 150 to 1000 picograms per ml. At levels below 150 pg/ml, vitamin $B_{12}$ deficient anaemia would be diagnosed. In the past, microbiological assays have been used, involving the organism *Euglena gracilis*. Recently, radioassays have been developed which employ intrinsic factor (hereinafter "IF") as the binding protein (see, for example, Clin. Chim. Acta, 32 (1971), 339). In these radioassays, it is essential first to treat the serum under assay to separate the $B_{12}$ from its serum binding protein transcobalamin (hereinafter "TC"). This is effected by diluting the serum in a low pH buffer and then boiling for about 15 minutes. The TC is thereby denatured but the $B_{12}$ is unaffected. The radioassay is then performed on the boiled serum.

Various shortcomings have been recognised in the use of IF as the binding protein in such radioassays and it has been suggested (British Journal of Haematology, 25 (1973), 359) that chicken serum (hereinafter "CS") would provide a more satisfactory binding protein for such purposes. In particular in that article, it is shown that, at relatively high pH's (9 up to 12), the binding of IF with $B_{12}$ falls off very sharply whereas the binding of CS with $B_{12}$ remains constant. On this basis, the authors recommend conducting the radioassay with CS at a pH of about 9.2. Furthermore, it is shown in the paper that the binding of $B_{12}$ with CS is unaffected by the presence of denatured human serum (as is produced in the essential preliminary radioassay step of boiling the serum to denature the endogenous $B_{12}$ binding protein).

Whilst the prior known radioassay procedure for assaying $B_{12}$ using IF can be improved by substituting CS as the binding protein, the procedure (even with CS) nevertheless suffers from a number of disadvantages, all basically deriving from the necessity for a dilution and boiling step. Thus, the values obtained for the $B_{12}$ concentration are normally higher (when the free fraction is counted) than those obtained (on the same sera) by the microbiological method. This may be due to non-specific adsorption of $B_{12}$ onto the serum protein denatured by boiling. The boiling step is itself undesirable since it is time-consuming and very difficult to effect on an automatic continuous basis. Furthermore, in order to prevent precipitation during boiling, a 1/5 dilution of the serum is required. The concentration of radio-label used is relatively high (often greater than some of the lower standards) and this, together with the requirement for a dilution step, results in poor sensitivity and lack of precision at the lower end of the scale. This is particularly important since it is the lower end of the scale, e.g. around and below 150 pg/ml, where the greatest accuracy is necessary.

We have now devised an improved method of assaying $B_{12}$ in liquids, particularly in human serum, by which certain disadvantages of the above-described radioassay procedures are reduced or overcome. In particular, we have found that if the assay is carried out using CS as the binding protein, at a pH of about 12.8 to 13.2, there is no necessity for any preliminary boiling of the human serum sample, or for any dilution thereof. The avoidance of the dilution and boiling step not only substantially simplifies the procedure, and renders it suitable for continuous flow techniques, but also improves the accuracy of the assay.

In one aspect, the invention provides a method of assaying a liquid for vitamin $B_{12}$, which comprises: forming a mixture comprising a sample of the liquid, vitamin $B_{12}$-binding proteins from chicken serum, and a buffer to provide a pH in the range 12.8 to 13.2, whereby vitamin $B_{12}$ in the mixture becomes bound to the said binding proteins, and then measuring the amount of vitamin $B_{12}$ present in the sample by analysis of a component of the mixture.

In one preferred embodiment, the invention provides a method of competitive binding assay for vitamin $B_{12}$ in a liquid, which comprises:

(a) forming a mixture comprising a sample of the liquid, vitamin $B_{12}$-binding proteins from chicken serum, labelled vitamin $B_{12}$, and a buffer to provide a pH of 12.8 to 13.2; the amount of said binding proteins from chicken serum being insufficient to bind with all the vitamin $B_{12}$ and labelled vitamin $B_{12}$ present.

(b) separating the free unbound fraction of vitamin $B_{12}$ and labelled vitamin $B_{12}$ in the mixture from the bound fraction of vitamin $B_{12}$ and labelled vitamin $B_{12}$ in the mixture; and (c) analysing the free or the bound vitamin $B_{12}$ and labelled vitamin $B_{12}$ fraction for its labelled vitamin $B_{12}$ content and thereby determining from standard results the amount of vitamin $B_{12}$ present in the sample.

When the method of the invention is used to assay $B_{12}$ in human sera, the buffer should contain an amount of cyanide ion sufficient to convert all the $B_{12}$ present in human serum into the cyano form. Normally, potassium cyanide is used although other sources of cyanide ion (such as sodium cyanide, for example) can be used. The cyano form of the $B_{12}$ is dissociable from its human serum binder at the high pH's used in the method of this invention. As the concentration of KCN in the assay buffer is increased from zero, so the dissociation of the $B_{12}$ from its human serum binder increases. At a KCN concentration of about 20 $\mu$g/ml, dissociation is greater than 92%. Above this concentration, there is only a slightly increased dissociation, but the binding of $B_{12}$ to CS becomes seriously impaired. It is, therefore, preferred in the method of the invention to include in the assay buffer KCN (for example) at a concentration of about 20 $\mu$g/ml.

At pH's of about 12.9 and above, $B_{12}$ is completely dissociated from the $B_{12}$ binding proteins (TC) present in human serum. At such pH's, however, we have found that $B_{12}$ is still bound to CS. By using CS as the binding protein at pH's of about 12.9 and above, therefore, there is no interference from human serum TC and the CS is still bound to $B_{12}$, giving high accuracy in the assay.

In the method of the invention, the pH is preferably from 12.9 to 13.1. Lower or higher pH's may be used (i.e. 12.8 or 13.2), but we have found that at about pH 12.7, the $B_{12}$ is not completely dissociated from the $B_{12}$ binding proteins in human serum. At pH's above about 13.1, the degree of binding between the CS and $B_{12}$ decreases.

In the method of the invention use is made of the $B_{12}$ binding proteins present in CS. Whole CS may be used or, if it is desired, the $B_{12}$ binding proteins thereof (which we believe to be CS transcobalamins) may be separated from CS and used as such. When whole CS is used, any native $B_{12}$ present therein will not interfere because (as will be clear to those skilled in the art), the CS is used at large dilutions (of the order of 10,000).

In the prior art, competitive binding radioassays have been used for $B_{12}$. In a competitive binding method of the present invention, a radioactive label is preferred (such as $^{57}Co$ or $^{125}I$) but other labels (such as fluorescent or enzyme labels, for example) may be used. The assay may be performed without using any label but this is not generally preferred since it normally entails far more work and is open to greater error. Hereinafter, the invention is described with reference to the use of a radiolabel ($^{57}Co$).

In a competitive binding method of the invention, it is necessary in step (b) to separate the free fraction $B_{12}$ (labelled and non-labelled) from the bound fraction $B_{12}$ (i.e. the labelled and non-labelled $B_{12}$ which has become bound to the chicken serum proteins). There are two alternative techniques which we prefer in order to facilitate this separation. In the first, the mixture is contacted with a solid material, conveniently a particulate material, which can selectively adsorb or bind to either the free $B_{12}$ fraction or the bound $B_{12}$ fraction (but not both). We have found that albumin-coated charcoal particles are suitable for this purpose (since they selectively adsorb the free fraction). Other particles may be used as will be clear to those skilled in the art. The solid material is then separated from the mixture and may itself be analysed for its labelled $B_{12}$ content, or the remaining mixture may be analysed.

The second, alternative, technique involves the use in step (a) of particulate material on which the chicken serum binding proteins have been immobilised. In this manner, the bound $B_{12}$ fraction itself is immobilised (upon becoming bound to the chicken serum proteins). The solid particles can then be separated from the mixture, carrying with them the bound (but not the free) $B_{12}$ fraction. Preferably, the particles comprise a magnetically attractable material so that they can readily be separated from the mixture. Details of the use of such particles are given in our British patent application No. 10089/76 to which reference should be made for further details.

Examples of these two techniques, in general terms, are given below in relation to the assay of human sera.

In the first technique, the human serum under assay is mixed with a solution of labelled $B_{12}$, for example $^{57}Co$-labelled $B_{12}$, and an extract of CS (containing $B_{12}$-binding proteins thereof) in a buffer at a pH of about 13. The mixture is incubated, and then albumin-coated charcoal is added. The coated charcoal adsorbs the free $B_{12}$ but not the complexes formed between the $B_{12}$ and the CS binding proteins. The charcoal is then separated and either the remaining liquid, or (more preferably) the separated charcoal, is assayed for $^{57}Co$. From results obtained assaying solutions of known concentration of $B_{12}$, the amount of $B_{12}$ in the human serum under assay can be determined from the $^{57}Co$ content thereof. (e.g. using standard curves).

In the second technique, the $B_{12}$-binding proteins from CS are immobilised on solid particulate matter. For example, they may be coupled to cellulose (or cellulose-coated) particles activated with CNBr. The technique of immobilising reactants on small particles is known in the art. We prefer to use particles containing a magnetically attractable material (such as $Fe_3O_4$) since the subsequent separation step is thereby facilitated. The particles are mixed with the human serum under assay and with labelled $B_{12}$, for example $^{57}Co$-$B_{12}$, and the mixture is shaken and incubated. Thereafter, the particles are separated and either the remaining liquid, or the separated particles, assayed for $^{57}Co$.

Whilst the method of the invention is particularly useful in the assay of human serum, it may also be used to assay the $B_{12}$ content of other liquids. Further, it may be used to assay chemical analogues of $B_{12}$ which bind with CS. It is to be understood, therefore, that in this specification and claims, reference to vitamin $B_{12}$ includes reference to close chemical analogues thereof which can also be assayed by the method of the invention.

The method of the invention can be carried out on a continuous flow basis (the general techniques of which are well known in the art).

In order that the invention may be more fully understood, the following Examples are given by way of illustration only. In the Examples, reference is made to the accompanying drawings in which.

EXAMPLE 1 (solid-phase assay)

The $B_{12}$-binder of CS is coupled to cellulose/$Fe_3O_4$ particles (average size 2–3 microns) by first activating the particles by the standard technique of CNBr-activation of the cellulose component, followed by incubation of the CS with the activated particles for 72 hours at 4° C. (approx.).

The buffer used in the assays, and for dilution of assay components prior to assay, is KCl 50 mM, KCN 0.002%, $NaN_3$ 0.1%, adjusted to pH 13.0 with NaOH, 2 N.

The $^{57}Co$-$B_{12}$ was purchased commercially and had a specific activity of 100 to 300 $\mu Ci/\mu g$.

The assay technique is as follows, in order of addition:

standard or serum: 50 $\mu L$ (microliters)

$^{57}Co$-$B_{12}$ (4.4 pg): 150 $\mu L$ solid-phase-CS: 100 $\mu L$

The solid-phase CS is used at a dilution of 1 gm in 640 ml, predetermined from a standard dose-response curve as the optimal dilution for the assay. The incubates are mixed continuously by end-over-end rotation, for 3 hours at room temperature. Separation is effected by centrifugation, the particles washed with buffer and the solid-phase (bound fraction) counted for 5 minutes in a gamma counter.

Figure 1:
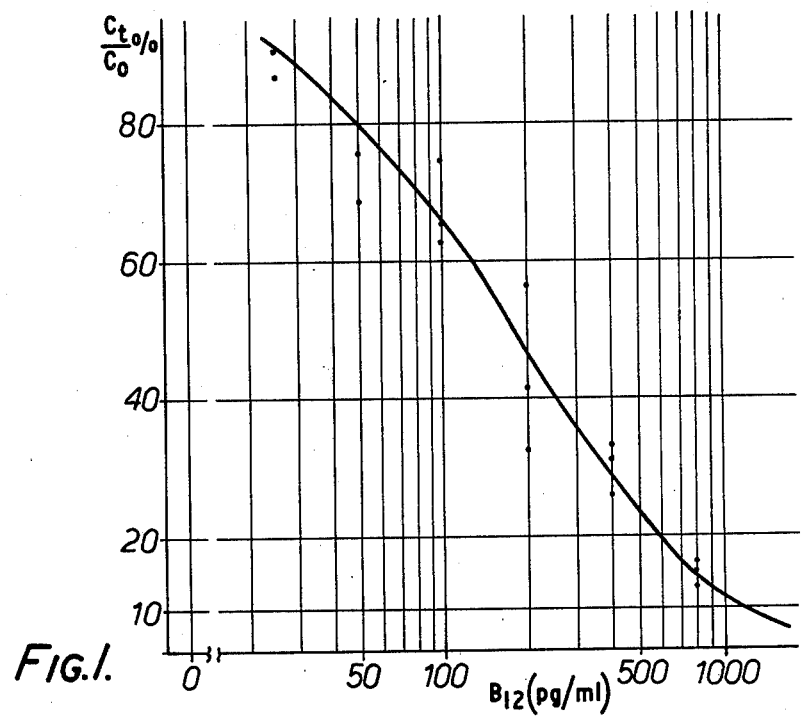
FIG. 1 is a standard curve for the assay of Example 1.

Using standard solutions of $B_{12}$, the standard curve shown in FIG. 1 of the accompanying drawings was obtained. Using this curve, 10 sera were assayed, and, relative to the *E. gracilis* microbioassay, correlated with a regression line of $y = 0.90x + 31$, and correlation coefficient of 0.93.

EXAMPLE 2 (Liquid-phase assay)

An extract of the $B_{12}$ binding protein was obtained from CS by the following method: $(NH_4)_2SO_4$ precipitation—that fraction of protein precipitating between 35% and 80% saturation. This fraction was redissolved in 10 mM $NH_4HCO_3$, applied to a column of DE-52 cellulose and eluted with a gradient of $NH_4HCO_3$. Aliquots of this extract were used in all subsequent liquid phase assays.

The buffer used in the assay, and for dilution of assay components prior to asssay, is KCl 50 mM, KCN 0.0002%, NaN$_3$ 0.1%, adjusted to pH 13.0 with NaOH 2 N.

The assay technique is as follows, in order of addition:

standard or serum: 50 μL
$^{57}$Co-B$_{12}$ (4.4 pg): 100 μL
buffer: 1250 μL
CS extract: 100 μL The CS extract is used at a dilution of 1/12,800, predetermined from a standard dose-response curve as the optimal dilution for the assay. After mixing the assay components, the incubates are allowed to stand at room temperature for 2 hours. Separation of the bound and free fractions is effected by addition of 0.3 ml of a charcoal suspension prepared as follows:

Norit-OL charcoal: 5 g/100 ml distilled water
Bovine serum albumin (BSA): 0.5 g/100 ml distilled water Mix these two together, centrifuge the BSA-coated charcoal to remove excess BSA and "fines" and resuspend the charcoal to original volume (200 ml). Add NaN$_3$ to a final concentration of 0.1%.

After charcoal addition, the assay tubes are mixed and centrifuged for 10 minutes at approx. 3000 RPM. The supernatant is aspirated and the charcoal pellet (free fraction) is counted for 5 minutes in a gamma counter.

Figure 2:
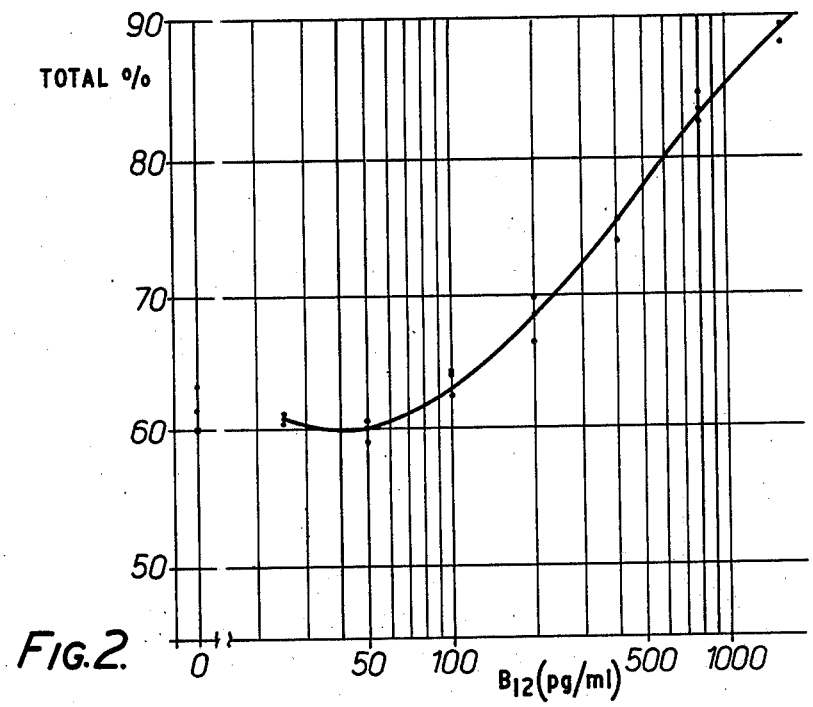
FIG. 2 is a standard curve for the assay of Example 2.
Figure 3:
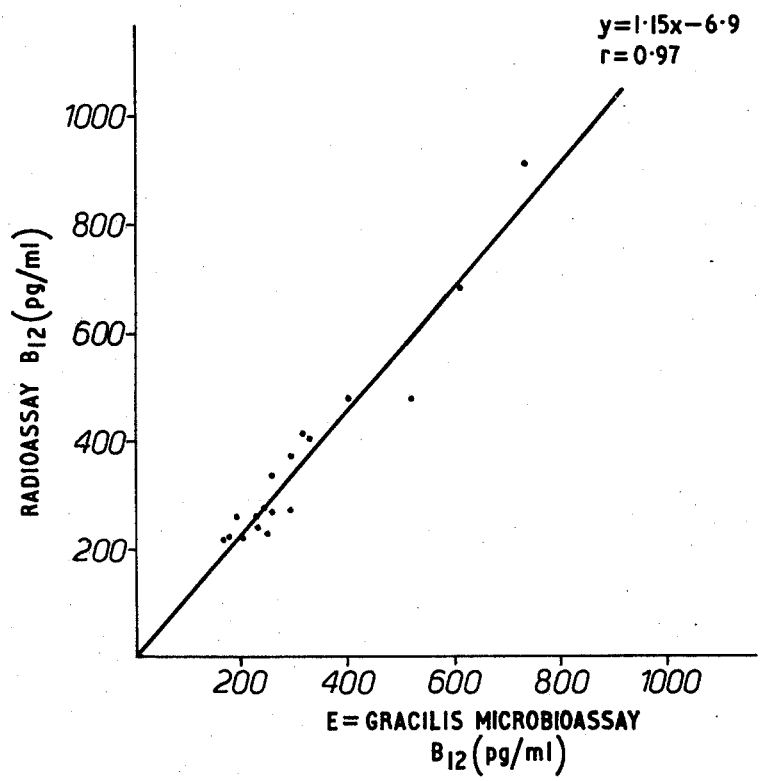
FIG. 3 is a correlation between the results obtained by the present invention (Example 2) and those obtained microbiologically.

Using standard solutions of B$_{12}$, the standard curve shown in FIG. 2 of the accompanying drawings was obtained. Using this curve, 20 human sera were assayed and results compared with assays by the microbiological method. A correlation coefficient of 0.97, with a regression line of y=1.15x−6.92, was obtained (FIG. 3).

The invention also includes a kit for carrying out a radioassay of B$_{12}$ by the method of the invention. Such a kit may, for example, comprise a range of B$_{12}$ standards, CS extract, quality control sera, and $^{57}$Co-B$_{12}$. These components may all be in freeze-dried form. The kit may also contain coated-charcoal suspension.

We claim:

1. A method of assaying a liquid for vitamin B$_{12}$, which comprises: forming a mixture comprising a sample of the liquid, vitamin B$_{12}$-binding proteins from chicken serum, and a buffer to provide a pH in the range 12.8 to 13.2, whereby vitamin B$_{12}$ in the mixture becomes bound to the said binding proteins; and then measuring the amount of vitamin B$_{12}$ present in the sample by analysis of a component of the mixture.

2. A method according to claim 1, wherein whole chicken serum is included in the mixture to provide the said binding proteins.

3. A method of competitive binding assay for vitamin B$_{12}$ in a liquid, which comprises:
    (a) forming a mixture comprising a sample of the liquid, vitamin B$_{12}$-binding proteins from chicken serum, labelled vitamin B$_{12}$, and a buffer to provide a pH of 12.8 to 13.2; the amount of said binding proteins from chicken serum being insufficient to bind with all the vitamin B$_{12}$ and labelled vitamin B$_{12}$ present;
    (b) separating the free unbound fraction of vitamin B$_{12}$ and labelled vitamin B$_{12}$ in the mixture from the bound fraction of vitamin B$_{12}$ and labelled vitamin B$_{12}$ in the mixture; and
    (c) analysing the free or the bound vitamin B$_{12}$ and labelled vitamin B$_{12}$ fraction for its labelled vitamin B$_{12}$ content and thereby determining from standard results the amount of vitamin B$_{12}$ present in the sample.

4. A method according to claim 3 wherein, in step (b), the mixture is contacted with a solid material which selectively binds to one only of said fractions, and after said binding the said material is separated from the mixture.

5. A method according to claim 4 wherein the said solid material comprises particles of albumin-coated charcoal which selectively adsorbs the free fraction.

6. A method according to claim 3 wherein in step (a), there is used vitamin B$_{12}$-binding proteins from chicken serum which proteins are immobilised on solid particulate material, and in step (b) the said particulate material, carrying the proteins and the bound fraction, is separated from the mixture.

7. A method according to claim 6 wherein the said particulate material, on which the binding proteins are immobilised, comprises a magnetically attractable material, and wherein in step (b) the said particulate material is separated from the mixture by use of a magnet.

8. A method according to claim 3 wherein in step (a), whole chicken serum is included in the mixture to provide said vitamin B$_{12}$-binding proteins.

9. A method according to claim 3 wherein the labelled vitamin B$_{12}$ comprises, as label, a radioactive atom.

10. A method according to claim 3 wherein the liquid under assay is human serum, and wherein the said buffer includes cyanide ion in an amount sufficient to convert all the vitamin B$_{12}$ in the human serum into the cyano form.

11. A method according to claim 10 wherein the assay is effected without subjecting the human serum to boiling.

12. A method according to claim 10 wherein the buffer provides a pH in the mixture of from 12.9 to 13.1.

13. A method according to claim 3 which is effected by continuous flow automated techniques.

* * * * *